(12) United States Patent  
Dahl et al.

(10) Patent No.: US 7,094,937 B2  
(45) Date of Patent: Aug. 22, 2006

(54) COMPOSITIONS COMPRISING CYCLOHEXAMANTANE

(75) Inventors: Jeremy E. Dahl, Palo Alto, CA (US); Robert M. Carlson, Petaluma, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 227 days.

(21) Appl. No.: 10/012,335

(22) Filed: Dec. 12, 2001

(65) Prior Publication Data

US 2002/0137976 A1 Sep. 26, 2002

Related U.S. Application Data

(60) Provisional application No. 60/262,842, filed on Jan. 19, 2001, provisional application No. 60/337,918, filed on Nov. 9, 2001, and provisional application No. 60/334,943, filed on Dec. 4, 2001.

(51) Int. Cl.  
*C07C 13/00* (2006.01)  
*C07C 7/04* (2006.01)  
*C07C 7/14* (2006.01)

(52) U.S. Cl. .................... 585/16; 585/21; 585/22; 585/812; 585/807; 585/809; 585/804; 585/803; 208/347

(58) Field of Classification Search ............ 585/16, 585/802, 812, 807, 809; 208/347  
See application file for complete search history.

(56) References Cited

U.S. PATENT DOCUMENTS

| | | | |
|---|---|---|---|
| 3,457,318 A | 7/1969 | Capaldi | |
| 3,832,332 A | 8/1974 | Thompson | |
| 4,952,747 A | 8/1990 | Alexander | |
| 4,952,748 A | 8/1990 | Alexander | |
| 4,952,749 A | 8/1990 | Alexander | |
| 4,982,049 A | 1/1991 | Alexander | |
| 5,017,734 A | 5/1991 | Baum | |
| 5,019,665 A | 5/1991 | Partridge | |
| 5,245,104 A | 9/1993 | Cullick | |
| 5,268,513 A | 12/1993 | Shen | |
| 5,298,666 A | 3/1994 | Shen | |
| 5,306,851 A | 4/1994 | Wu | |
| 5,347,063 A | 9/1994 | Shen | |
| 5,369,213 A | 11/1994 | Shen | |
| 5,380,947 A | 1/1995 | Chen | |
| 5,382,684 A | 1/1995 | Moini | |
| 5,397,488 A | 3/1995 | Chen | |
| 5,410,092 A | 4/1995 | Shen | |
| 5,414,189 A | 5/1995 | Chen | |
| 5,430,193 A | 7/1995 | Shen | |
| 5,461,184 A | 10/1995 | Swanson | |
| 5,498,812 A | 3/1996 | Bradway | |
| 5,576,355 A | 11/1996 | Chen | |
| 6,235,851 B1 | 5/2001 | Ishii | |

FOREIGN PATENT DOCUMENTS

EP 0399851 11/1996  
WO WO 95/11472 4/1995

OTHER PUBLICATIONS

STN Registry 137695-69-3, Dec. 6, 1991, pp. 1-3.*

(Continued)

*Primary Examiner*—Glenn Caldarola  
*Assistant Examiner*—Tam M. Nguyen  
(74) *Attorney, Agent, or Firm*—Burns, Doane, Swecker & Mathis, L.L.P.

(57) ABSTRACT

Disclosed are compositions comprising $C_{26}H_{30}$ hexamantane, referred to herein as peri-condensed hexamantane, fully condensed hexamantane, and cyclohexamantane. These enriched cyclohexamantane compositions comprise at least 5 percent by weight cyclohexamantane based upon the total weight of the composition.

5 Claims, 14 Drawing Sheets

OTHER PUBLICATIONS

Shen, Mingzuo et al., "Finite Td Symmetry Models for Diamond: From Adamantane to Super–Adamantane (C35H36)", Chemical Abstracts Service, Columbus, OH, No. 116:40599 CA XP002201142 & J Am Chem. Soc., 114:2, pp. 497–505 (1992).

Aczel, et al., "Stability of Adamantane and its Derivatives to Coal–liquefaction Conditions, and its implications toward the organic structure of Coal", *Fuel*, vol. 58, pp. 228–230, (Mar. 1979).

Balaban, et al., Systemic Classification and Nomenclature of Diamond Hydrocarbons–I, *Tetrahedron*, 34, pp. 3599–3606, (1978).

Badziag, P., et al., "Nanometre–sized Diamonds are More Stable than Graphite", *Nature*, vol. 343, pp. 244–245, and 517.

Bagrii, Ye, et al., "Catalytic Breakdown of Paraffinic Hydrocarbons in the Presence of Adamantanes", *Petrol. Chem USSR*, vol. 30, No. 2, pp. 131–134, (1990).

Chung, et al., Recent Development in High–Energy Density Liquid Fuels, *Energy and Fuels*, 13, pp. 641–649, (1999).

Dahl, J., et al., Diamondoid Hydrocarbons as Indicators of Natural Oil Cracking, *Nature*, 399, pp. 54–57, (1999).

Drexler, Eric K., *Nanosystems: Molecular Machinery Manufacturing and Computation*, John Wiley & Sons, pp. 238–249, (1992).

Fort, Jr., et al., Adamantane: Consequences of the Diamondoid Structure, *Chem. Rev.*, 64, pp. 277–300, (1964).

Hala, V.S., et al., "Analyse Unds erwendung on Pyrolyseol", *Jahrgang*, pp. 85–87, (Feb. 1971) In German– English Abstract on p. 85.

Landa, S., "Adamantane and Its Homologues", *Current Science*, Gangalore, India, Vo. 32, pp. 485–489 (1963).

Lin, et al., Natrual Occurrence of Tetramantane ($C_{22}H_{36}$), Pentamantane ($C_{26}H_{32}$), and Hexamantane ($C_{30}H_{36}$) in a Deep Petroleum Reservoir, *Fuel*, 74:10, pp. 1512–1521, (1995).

McKervey, Synthetic Approaches to Large Diamondoid Hydrocarbonds, *Tetrahedron*, 36, pp. 971–992, (1980).

Machacek, V., et al., "Let Od Objeveni Adamantanu", *Chemicke Listy/svazek*, pp. 753–761, (1982) Russian—English Abstract on p. 761.

Oya, A, et al., "Carbonization of Adamantanes to a Graphitizable Carbon", *Fuel*, vol. 60, pp. 667–669, (Aug. 1981).

Petrov, A., "Hydrocarbons of Adamantane Series as Indicies of Petroleum Catagenesis Process", *Advances in Organic Geo Chemistry*, $6^{th}$ International Meeting on Organic Geochemistry, pp. 517–522 (1973).

Prusova, D., Liquid Chromatography of Adamantanes and Carbon Adsorbents, *J. Chrom*, 234, pp. 1–11, (1982).

Rollman, L., et al., "Adamantanes From Petroleum, with Zeolites", American Chemical Study, $210^{th}$ ACS National Meeting, Abstract and paper, Aug. 20, 1995).

Sandia National Laboratories (2000), World's First Diamond Micromachines Created at Sandia, Press Release, (Feb. 22, 2000), www.Sandia.gov.

Schleyer, P., et al., "Nonacyclo[$11.7.1.1^{2,18}.0^{3,16}.0^{4,13}.0^{5,10}.0^{6,14}.0^{7,11}.0^{15,20}$]–Docosane, a Bastard Tetramantane", *J. of the Am. Chem. Soc.*, 90:8, letter to the editor, Aug. 28, 1968.

Shen, M., et al., Finite $T_d$ Symmetry Models for Diamond: From Adamantane to Superadamantane ($C_{35}H_{36}$), *J. Am., Chem. Soc.*, vol. 114, No. 2, pp 497–505, (1992).

Supryadkina, NY, et al., "Catalytic Dealkylation of Alkyladamantanes", *Petrol. Chem., USSR*, vol. 28, No. 2, pp. 103–110, (1988).

Tominaga, K., et al., "Next–generation Fine Chemicals Raw Material–Adamantane", *Chem Econ & Eng. Review*, vol. 17, No. 10, pp. 23–29, (Oct. 1985).

Vodicka, L, et al., "High Performance Liquid Chromatography of Halogeno Derivatives of Adamantane and Diamantane", *J. Chrom*, 270, pp. 199–205, (1983).

Wingert, W., "G.c.–m.s. Analysis of Diamondoid Hydrocarbons in Smackover Petroleums", *Fuel*, vol. 71, pp. 37–42, (Jan. 1992).

* cited by examiner

| | |
|---|---|
| Name: | [12312] Hexamantane |
| | Cyclohexamantane |
| Formula: | $C_{26}H_{30}$ |
| Molecular Weight | 342.526 |
| Molecular Weight (Exact) | 342.2347511 |
| Symmetry | $D_{3d}$ |

Carbon Framework

CPK Representations

[12312] Hexamantane (Cyclohexamantane)
View into Specified Diamond Crystal Lattice Plane

| 111 | 110 | 100 |
|---|---|---|
|  |  |  |
|  |  |  |
|  |  | |
|  |  | |

- Feedstock B
- Feedstock A

A)

Cyclohexamantane, & Pentamantanes

Product

Time (min)

B)

Starting Material

GC Time →

FIG. 11

| ODS HPLC Fraction # | 1 | 2 | 3 | 4 | 5 | 6 | 7 | 8 | 9 | 10 | 11 | 12 | 13 | 14 | 15 | 16 | 17 | Fully Condensed Hexamantane |
|---|---|---|---|---|---|---|---|---|---|---|---|---|---|---|---|---|---|---|
| 23 | | | | | | | | | | | | | | | | | | ■ Cyclohexamantane |
| 24 | | | | | | | | | | | | | | | | | | ■ |
| 25 | | | | | | | | | | | | | | | | | | ■ |
| 26 | | | | | | | | | | | | | | | | | | ■ |
| 27 | | | | | | | | | | | | | | | | | | |

A)

B)

A)

B)

Cyclohexamantane precipitant
From HPLC 18 Fraction 23-26
(precipitant formed as fraction was being
concentrated for injection in HPLC 37)

A)

B)

A)

B)

Cyclohexamantane crystals from
HPLC 37 Fraction 6-9

COMPOSITIONS COMPRISING CYCLOHEXAMANTANE

REFERENCE TO RELATED APPLICATIONS

This application claims priority under 35 U.S.C. §119(e) to U.S. Provisional Application No. 60/262,842, filed Jan. 19, 2001 and to U.S. Provisional Application No. 60/337,918, filed Nov. 9, 2001, both of which are incorporated by reference. This application also claims priority under 35 U.S.C. §119(e) to U.S. Provisional Application No. 60/334,943, filed Dec. 4, 2001.

BACKGROUND OF THE INVENTION

1. Field of the Invention

Embodiments of the present invention are directed toward novel compositions comprising the $C_{26}H_{30}$ hexamantane herein referred to as "cylcohexamantane."

2. References

The following publications and patents are cited in this application as superscript numbers:

[1] Lin, et al., *Natural Occurrence of Tetramantane $(C_{22}H_{28})$, Pentamantane $(C_{26}H_{32})$ and Hexamantane $(C_{30}H_{36})$ in a Deep Petroleum Reservoir*, Fuel, 74(10):1512–1521 (1995)

[2] Alexander, et al., *Purification of Hydrocarbonaceous Fractions*, U.S. Pat. No. 4,952,748, issued Aug. 28, 1990

[3] McKervey, Synthetic *Approaches to Large Diamondoid Hydrocarbons*, Tetrahedron, 36:971–992 (1980).

[4] Wu, et al., *High Viscosity Index Lubricant Fluid*, U.S. Pat. No. 5,306,851, issued Apr. 26, 1994.

[5] Chung et al., *Recent Development in High-Energy Density Liquid Fuels*, Energy and Fuels, 13, 641–649 (1999).

[6] Sandia National Laboratories (2000), *World's First Diamond Micromachines Created at Sandia*, Press Release, (2/22/2000) www.Sandia.gov.

[7] Balaban et al., Systematic *Classification and Nomenclature of Diamondoid Hydrocarbons—I*, Tetrahedron. 34, 3599–3606 (1978).

[8] Chen, et al., *Isolation of High Purity Diamondoid Fractions and Components*, U.S. Pat. No. 5,414,189, issued May 9, 1995

All of the above publications and patents are herein incorporated by reference in their entirety to the same extent as if each individual publication or patent was specifically and individually indicated to be incorporated by reference in its entirety.

3. State of the Art

Hexamantanes are bridged-ring cycloalkanes. They are the hexamers of adamantane (tricyclo[3.3.1.1$^{3,7}$]decane) or $C_{10}H_{16}$, in which various adamantane units are face-fused. The compounds have a "diamondoid" topology, which means their carbon atom arrangement is superimposable on a fragment of the diamond lattice (FIG. 1). Hexamantanes possess six of the "diamond crystal units" and therefore, it is postulated that there are thirty-nine possible hexamantane structures. Among them, twenty-eight of the thirty-nine have the stoichiometric formula $C_{30}H_{36}$ (molecular weight 396 Daltons) and of these, six are symmetrical, having no enantiomers. Ten of the thirty-nine hexamantanes have the stoichiometric formula $C_{29}H_{34}$ (molecular weight 382 Daltons).

The remaining hexamantane (FIGS. 2 and 3) is fully condensed, has the stoichiometric formula $C_{26}H_{30}$ (molecular weight 342 Daltons), and compositions comprising this hexamantane are the subject matter of the embodiments of this invention.

Very little has been published pertaining to the hexamantanes in general, and cyclohexamantane in particular. Hexamantane compounds have not been artificially synthesized, and these compounds have been recently thought to have only a theoretical existence.[1,7] Academic chemists have primarily focused research on the interplay between physical and chemical properties in the lower diamondoids such as adamantane, diamantane and triamantane. Adamantane and diamantane, for instance, have been studied to elucidate structure-activity relationships in carbocations and radicals.[3] Process engineers have directed efforts toward removing lower diamondoids from hydrocarbon gas streams.[2] Lower diamondoids can cause problems during the production of natural gas by solidifying in pipes and other pieces of related processing equipment.

The literature contains little information regarding the practical applications of hexamantanes. This fact is probably due to extreme difficulties encountered in their isolation and due to failed synthesis attempts. Lin and Wilk, for example, discuss the possible presence of pentamantanes in a gas condensate and further postulate that hexamantanes may also be present.[1] The researchers postulate the existence of the compounds based on a mass spectrometric fragmentation pattern. They did not, however, report the isolation of a single pentamantane or hexamantane. Nor were they able to separate non-ionized components during their spectral analysis. McKervey et al. discuss an extremely low-yielding synthesis of anti-tetramantane.[3] The procedure involves complex starting materials and employs drastic reaction conditions (e.g., gas phase on platinum at 360° C.). Although one isomer of tetramantane, i.e., anti-, has been synthesized through a double homologation route, these syntheses are quite complex reactions with large organic molecules in the gas phase and have not led to the successful synthesis of other tetramantanes. Similar attempts using preferred ring starting materials in accordance with the homologation route, have likewise failed in the synthesis of pentamantanes. Likewise, attempts using carbocation rearrangement routes employing Lewis acid catalysts, useful in synthesizing triamantane and lower diamondoids, have been unsuccessful in synthesizing tetramantanes or pentamantanes. Attempts to synthesize hexamantanes have also failed.

Among other properties, diamondoids have by far the most thermodynamically stable structures of all possible hydrocarbons that possess their molecular formulas due to the fact that diamondoids have the same internal "crystalline lattice" structure as diamonds. It is well established that diamonds exhibit extremely high tensile strength, extremely low chemical reactivity, electrical resistivity greater than aluminum oxide (alumina, or $Al_2O_3$), excellent thermal conductivity, a low coefficient of friction, and high x-ray transmissivity.

In addition, based on theoretical considerations, cyclohexamantane has a size in the nanometer range and, in view of the properties noted above, the inventors contemplate that such a compound would have utility in micro- and molecular-electronics and nanotechnology applications. In particular, the rigidity, strength, stability, variety of structural forms and multiple attachment sites shown by this molecule makes possible accurate construction of robust, durable, precision devices with nanometer dimensions. The various hexamantanes are three-dimensional nanometer sized units showing different diamond lattice arrangements.

This translates into a variety of rigid shapes and sizes for the thirty-nine hexamantanes. For example, [12121] hexamantane is rod shaped, [121(3)4] hexamantane has a "T" shaped structure while [12134] is "L" shaped and [1(2)3(1)2] is flat with four lobes. The two enantiomers of [12131] have left and right handed screw like structures. Cyclohexamantane ([12312] hexamantane) is disc- or wheel-shaped.

It has been estimated that MicroElectroMechanical Systems (MEMS) constructed out of diamond should last 10,000 times longer then current polysilicon MEMS, and diamond is chemically benign and would not promote allergic reactions in biomedical applications.[6] Again, the inventors contemplate that cyclohexamantane would have similar attractive properties. Applications of cyclohexamantane include molecular electronics, photonics, nanomechanical devices, and nanostructured polymers and other materials.

Notwithstanding these advantages of hexamantanes in general and cyclohexamantane in particular, the art, as noted above, fails to provide compositions comprising cyclohexamantane, or processes that would lead to these compositions. In view of the above, there is an ongoing need in the art to provide compositions comprising the $C_{26}H_{30}$ hexamantane herein referred to as cyclohexamantane.

SUMMARY OF THE INVENTION

Embodiments of the present invention are directed toward novel compositions comprising the $C_{26}H_{30}$ hexamantane herein referred to as either peri-condensed hexamantane, fully-condensed hexamantane, or cyclohexamantane.

Accordingly, embodiments of the present invention are directed toward a composition comprising at least about 5 percent by weight cyclohexamantane based on the total weight of the composition.

In another embodiment, the composition comprises cyclohexamantane in a range from about 50 to 100 weight percent, preferably about 70 to 100 weight percent, more preferably about 90 to 100 weight percent, and even more preferably about 95 to 100 weight percent based on the total weight of the composition.

When such compositions are sufficiently enriched in cyclohexamantane, the composition may form a crystalline structure. Accordingly, another embodiment of the present invention is directed toward a composition comprising cyclohexamantane in crystalline form.

BRIEF DESCRIPTION OF THE DRAWINGS

FIG. 1 illustrates the correlation of the structures of diamondoids to subunits of the diamond crystal lattice.

FIG. 10B illustrates the GC (DB-17 equivalent column) of Feedstock B atmospheric distillation fraction #5, exemplified in Example 1, which was used as feedstock in pyrolytic processing. FIG. 10A illustrates the GC of the product of the pyrolytic process.

FIG. 11 illustrates results of a preparative HPLC separation of Feedstock B distillate cut pyrolysis product saturated hydrocarbon fraction showing BPLC fractions taken using octadecyl silane "ODS" columns and acetone mobile phase. The "x" marks the fraction containing the highest concentration of cyclohexamantane.

DETAILED DESCRIPTION OF THE INVENTION

Embodiments of the present invention are directed toward $C_{26}H_{30}$ hexamantane compositions. However, prior to describing this invention in further detail, the following terms will first be defined.

Definitions

As used herein, the following terms have the following meanings.

The term "diamondoid" refers to substituted and unsubstituted caged compounds of the adamantane series including adamantane, diamantane, triamantane, tetramantane, pentamantane, hexamantane, heptamantane, octamantane, nonamantane, decamantane, undecamantane, and the like, and also including molecular weight forms of these components including isomers and stereoisomers of these forms. Substituted diamondoids preferably comprise from 1 to 10 and more preferably 1 to 4 substituents independently selected from the group consisting of alkyl, including straight chain alkyl, branched alkyl, or cycloalkyl groups.

Figure 1:
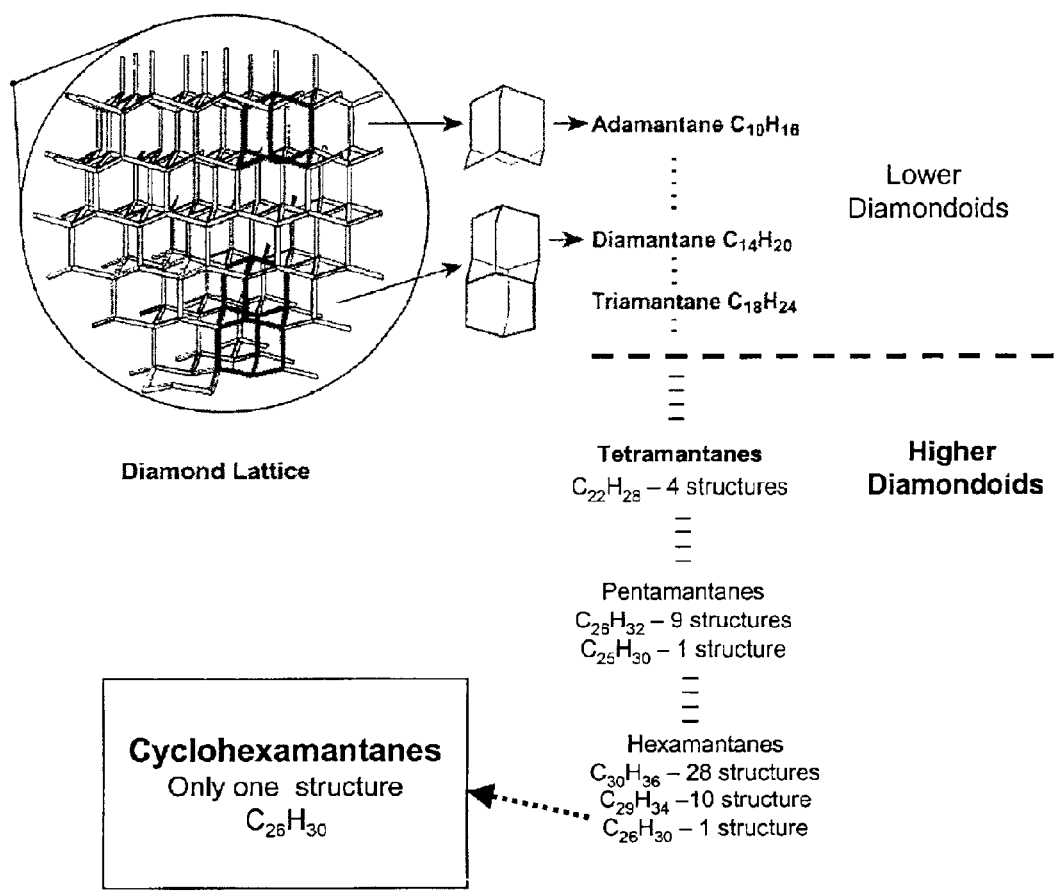
FIG. 1 illustrates the cage-shaped structure of diamondoids and their correlation to diamonds. Specifically.
Figure 2:
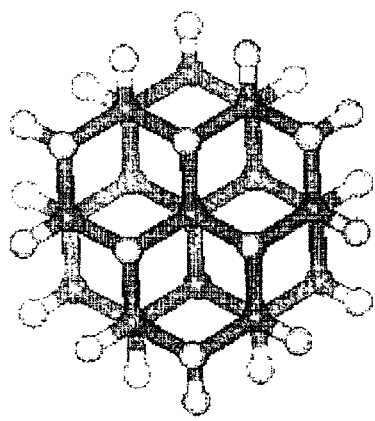
FIG. 2 illustrates the Ball and Stick, CPK and Carbon Framework representations of cyclohexamantane.
Figure 2:
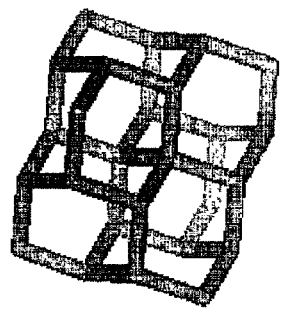
Figure 2:
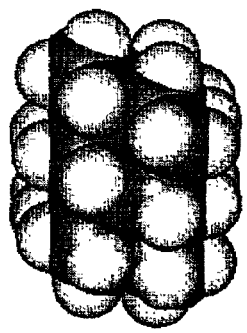
Figure 2:
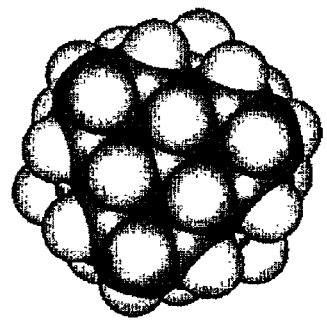
Figure 3:
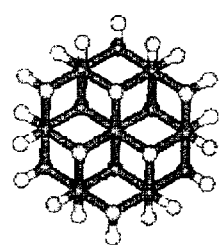
FIG. 3 illustrates the structure with views normal to various diamond crystal lattice planes of cyclohexamantane.
Figure 3:
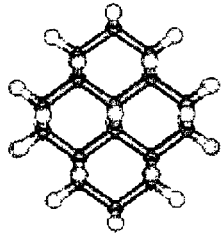
Figure 3:
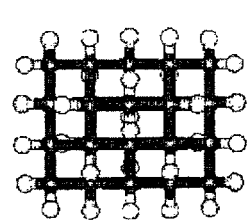
Figure 3:
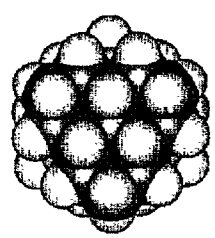
Figure 3:
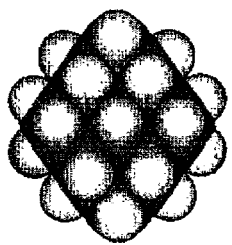
Figure 3:
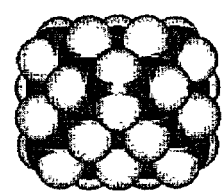
Figure 3:
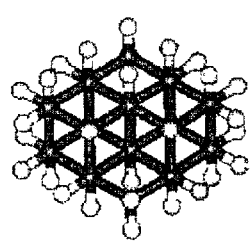
Figure 3:
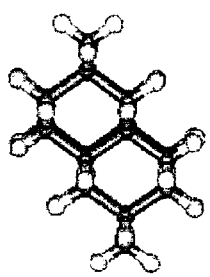
Figure 3:
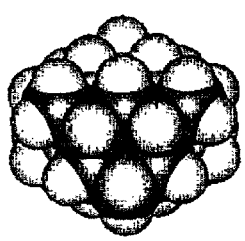
Figure 3:
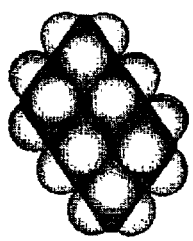

Hexamantanes are bridged-ring cycloalkanes. They are the hexamers of adamantane (tricyclo[3.3.1.1$^{3,7}$]decane) or C H$_{16}$ in which various adamantane units are face-fused. The compounds have a "diamondoid" topology, which means their carbon atom arrangement is superimposable on a fragment of the diamond lattice (FIG. 1). Thirty-nine possible hexamantane structures have been postulated by the inventors. Among them, twenty-eight of the thirty-nine have the molecular formula $C_{30}H_{36}$ (molecular weight 396 Daltons) and of these, six are symmetrical, having no enantiomers. Ten of the thirty-nine hexamantanes have the molecular formula $C_{29}H_{34}$ (molecular weight 382), and the remaining hexamantane (FIGS. 2 & 3) is the fully condensed hexamantane having the molecular formula $C_{26}H_{30}$ (molecular weight 342).

The term "cyclohexamantane" refers to fully condensed hexamantane having a molecular formula of $C_{26}H_{30}$. Preferably, cyclohexamantane is in non-ionized form.

The term "lower diamondoid components" or "adamantane, diamantane and triamantane components" refers to any and/or all unsubstituted and substituted derivatives of adamantane, diamantane and triamantane. These lower diamondoid components show no isomers and are readily synthesized, distinguishing them from the "higher diamondoid components."

The term "higher diamondoid components" refers to any and/or all substituted and unsubstituted tetramantane components; to any and/or all substituted and unsubstituted pentamantane components; to any and/or all substituted and unsubstituted hexamantane components; to any and/or all substituted and unsubstituted heptamantane components to any and/or all substituted and unsubstituted octamantane components; to any and/or all substituted and unsubstituted nonamantane components; to any and/or all substituted and unsubstituted decamantane components; to any and/or all substituted and unsubstituted undecamantane components; as well as mixtures of the above as well as isomers and stereoisomers of tetramantane, pentamantane, hexamantane, heptamantane, octamantane, nonamantane, decamantane, undecamantane, and the like.

The term "feedstock" or "hydrocarbonaceous feedstock" refers to hydro-carbonaceous materials comprising recoverable amounts of cyclohexamantane. Preferably, such feedstocks include oil, gas condensates, refinery streams, reservoir rocks, oil shale, tar sands, source rocks, and the like. Such feedstocks typically, but not necessarily, comprise one or more lower diamondoid components as well as non-diamondoid components. The feedstock is typically characterized as comprising components having a boiling point both below and above tetramantane which boils at about 350° C. at atmospheric pressure and more preferably, having a boiling point below and above cyclohexamantane. Typical feedstocks may also contain impurities such as sediment, metals including nickel, vanadium, and other inorganics. They may also contain heteromolecules containing sulfur, nitrogen and the like. Such feedstocks may be subsequently treated or subjected to various unit operations to alter the characteristics of the original feedstock and therein retain properties of said treated feedstock.

The term "remove" or "removing" refers to processes for removal of nondiamondoid components and/or lower diamondoid components from the feedstock. Such processes include, by way of example only, size separation techniques, distillation, evaporation either under normal or reduced pressure, well head separators, sorption, chromatography, chemical extraction, crystallization and the like. For example, Chen, et al.[8] disclose distillation processes for removing adamantane, substituted adamantane, diamantane, substituted diamantane, and triamantane from a hydrocarbonaceous feedstock. Size separation techniques include membrane separations, molecular sieves, gel permeation, size exclusion chromatography and the like.

The term "distillation" or "distilling" refers to atmospheric, reduced pressure distillation, and elevated pressure distillation processes on the hydrocarbonaceous feedstock which are conducted to concentrate cyclohexamantane by removal of other components from the feedstock. Unless otherwise specified, distillation temperatures are reported as atmospheric equivalents.

The term "thermal processing to pyrolyze" refers to either atmospheric, reduced pressure or elevated pressure heating of the feedstock to pyrolyze a portion of one or more components in the feedstock.

The term "nondiamondoid components of a feedstock" refers to components of the feedstock that are not diamondoid in character wherein the term "diamondoid" is as defined herein.

The term "chromatography" refers to any of a number of well known chromatographic techniques including, by way of example only, column or gravity chromatography (either normal or reverse phase), gas chromatography, high performance liquid chromatography, and the like.

The term "alkyl" refers to straight and branched chain alkyl groups typically having from 1 to 20 carbon atoms, more preferably 1 to 6 atoms, as well as cyclic alkyl groups typically having from 3 to 20 carbon atoms and preferably from 3 to 6 carbon atoms. This term also includes the intramolecular alkyl ring closures between two attachment sites on a higher diamondoid component. The term "alkyl" is exemplified by groups such as methyl, ethyl, propyl, butyl, isopropyl, isobutyl, sec-butyl, t-butyl, n-heptyl, octyl, cyclopropyl, cyclobutyl, cyclopentyl, cyclohexyl, and the like.

Methodology

The compositions of this invention can be obtained from readily available starting materials using the following general methods and procedures. It will be appreciated that where typical or preferred process conditions (i.e., reaction temperatures, times, solvents, pressures, etc.) are given, other process conditions can also be used unless otherwise stated. Optimum reaction conditions may vary with feedstocks, but such conditions can be determined by one skilled in the art by routine optimization procedures. Detailed methods for processing feedstocks to obtain higher diamondoid compositions are set forth in U.S. Provisional Patent Application No. 60/262,842 filed Jan. 19, 2001; U.S. Provisional Patent Application No. 60/300,148 filed Jun. 21, 2001; U.S. Provisional Patent Application No. 60/307,063 filed Jul. 20, 2001 and U.S. Provisional Patent Application No. 60/377,918 filed Nov. 9, 2001, entitled "Compositions Comprising Cyclohexamantane and Processes for their Isolation. These applications are herein incorporated by reference in their entirety.

To obtain the cyclohexamantane compositions described herein, a feedstock is selected such that the feedstock comprises recoverable amounts of cyclohexamantane. Preferably, such a feedstock comprises at least about 1 ppb (parts per billion) of cyclohexamantane. It is understood, of course, that feedstocks having higher concentrations of cyclohexamantane facilitate recovery.

Preferred feedstocks include, for example, natural gas condensates and refinery streams having high concentrations of higher diamondoids. With regard to the latter, such refinery streams include hydrocarbonaceous streams recoverable from cracking processes, distillations, coking and the like. Particularly preferred feedstocks include gas condensates feedstocks recovered from the Norphlet formation in the Gulf of Mexico and from the LeDuc formation in Canada.

The feedstocks used to obtain the compositions of this invention typically comprise nondiamondoid components having a boiling point both below and above cyclohexamantane as well as one or more lower diamondoid components and in such feedstocks, cyclohexamantane cannot be effectively recovered. Accordingly, a sufficient amount of these contaminants is removed from the feedstock under conditions to provide a treated feedstock from which cyclohexamantane can be recovered.

The removal of contaminants including lower diamondoids, and in many cases some noncyclohexamantane higher diamondoids and/or hydrocarbonaceous nondiamondoid material include, by way of example only, size separation techniques such as membranes, molecular sieves, etc., evaporation and thermal separators either under normal or reduced pressures, extractors, electrostatic separators, crystallization, chromatography, well head separators, and the like. A preferred separation method typically includes distillation of the feedstock to remove nondiamondoid components as well as lower diamondoid components, and in many cases some noncyclohexamantane higher diamondoids having a boiling point less than that of cyclohexamantane. Preferably, the feedstock is distilled to provide cuts above and below about 335° C., atmospheric equivalent boiling point, more preferably, above and below about 345° C. atmospheric equivalent boiling point and more preferably, above and below about 370° C. atmospheric equivalent boiling point. In either instance, the lower cuts, which are enriched in lower diamondoids and low boiling point higher diamondoid and nondiamondoid materials, are discarded or used to recover other higher diamondoids contained therein. Distillation can be operated to provide several cuts in the temperature range of interest to provide the initial isolation of the identified higher diamondoid. The cuts, which are enriched in higher diamondoids or the diamondoid of interest, are retained and may require further purification. For recovery of cyclohexamantane, the preferred distillation cuts are taken at atmospheric equivalent boiling point temperatures of from about 330 to 550° C., preferably from about 390 to 470° C. Additional temperature refinements will allow for higher purity cuts for concentration of cyclohexamantane. Other methods for the removal of contaminants and farther purification of an enriched cyclohexamantane fraction can additionally include the following non-limiting examples: size separation techniques, evaporation either under normal or reduced pressure, sublimation, crystallization, chromatography, well head separators, flash distillation, fixed and fluid bed reactors, reduced pressure, and the like.

The contaminant removal may also include a pyrolysis step either prior or subsequent to distillation. Pyrolysis is an effective method to remove hydrocarbonaceous, nondiamondoid components from the feedstock. It is effected by heating the feedstock under vacuum conditions or in an inert atmosphere, at a temperature of at least about 390° C. or 400° C. (preferably about 410° C. to about 475° C., most preferably about 410° C. to about 450° C. for from 5 to 30 hours. The specific conditions employed are selected such that recoverable amounts of cyclohexamantane are retained in the feedstock. The selection of such conditions is well within the skill of the art. Preferably, pyrolysis is continued for a sufficient period of time and at a sufficiently high enough temperature to thermally degrade at least about 10 percent by weight of the nondiamondoids components of the feed material prior to pyrolysis. More preferably at least 50 percent by weight, and even more preferably at least 90 percent by weight of the nondiamondoids are thermally degraded.

Pyrolysis, while a preferred embodiment, is not always necessary to facilitate the recovery, isolation or purification of cyclohexamantane. Other separation methods may allow for the concentration of cyclohexamantane to be sufficiently high in certain feedstocks that direct purification methods such as chromatography including preparative gas chromatography and high performance liquid chromatography, crystallization, and fractional sublimation may be used to isolate cyclohexamantane.

Even after distillation or pyrolysis/distillation, further purification of cyclohexamantane may be desired to provide the compositions of this invention. One may use purification techniques such as chromatography, crystallization, thermal diffusion techniques, zone refining, progressive recrystalization, size separation and the like. For instance, in one process, the recovered feedstock is subjected to the following additional procedures: 1) gravity column chromatography using silver nitrate impregnated silica gel; 2) two-column preparative capillary gas chromatography to isolate cyclohexamantane; or alternatively, one or multiple column high performance liquid chromatography; 3) crystallization to provide crystals of highly concentrated cyclohexamantane.

An alternative process is to use liquid chromatography including high performance liquid chromatography to isolate cyclohexamantane. As above, multiple columns with different selectivity can be used. Further processing using these methods allow for more refined separations which can lead to substantially pure cyclohexamantane.

Compositions

Accordingly, in one embodiment of the present invention, the composition comprises at least about 5 percent by weight cyclohexamantane based upon the total weight of the composition.

In another embodiment, the composition comprises cyclohexamantane ranging from about 50 to 100 percent by weight, preferably about 70 to 100 percent by weight, more preferably about 90 to 100 percent by weight, and even more preferably about 95 to 100 percent by weight based upon the total weight of the composition.

In another embodiment, the composition comprise from about 70 to 100 percent by weight, more preferably from about 90 to 100 percent by weight, even more preferably from about 95 to 100 percent by weight, and most preferably from about 99 to 100 percent by weight of the single cyclohexamantane component.

When such compositions are sufficiently enriched in cyclohexamantane, the composition may form a crystalline structure. Accordingly, another embodiment of the present invention is directed toward a composition comprising cyclohexamantane in crystalline form.

Utility

The compositions of the present invention comprise cyclohexamantane. These compositions are useful in micro- and molecular-electronics and nanotechnology applications.

In particular, the rigidity, strength, stability, variety of structural forms and multiple attachment sites shown by cyclohexamantane makes possible accurate construction of robust, durable, precision devices with nanometer dimensions. These special structural characteristics set these compounds apart from acyclic molecules, from condensed ring systems and even from bridged ring counterparts. The great stability, nanometer size, variable yet rigid 3-dimensional geometries, well defined distances for places of attachment and nonplanar bridgeheads lead to their unique features. Such features make compositions comprising cyclohexamantane useful in nanotechnology applications. In recent years there has been a rapidly rising interest in synthesizing large assemblies of organic molecules that might be able to serve as scaffolding structures in efforts to construct molecular objects of nanometer sized dimensions. Due to rigidity and special geometries of cyclohexamantane it is expected that molecular aggregates and molecular building blocks based upon such compositions will enable the construction and synthesis of an unprecedented array of desirable materials that may find applications in molecular electronic and computing devices, miniaturized machinery such as molecular robotics and self replicated manufacturing systems, or simply as novel materials with special chemical, optical, electrical, and thermal properties for coatings, film layering, and other applications taking advantage of the diamond-like properties of these compositions.

In addition, cyclohexamantane containing compositions can also be used in a high quality lubricating fluid which exhibits a high Viscosity Index and a very low pour point.[4] When so employed, these fluids comprise a fluid of lubricating viscosity and from about 0.1 to 10 weight percent cyclohexamantane.

Still further, these cyclohexamantane containing compositions can be used as high density fuels in the manner described by Chung, et al.[5], incorporated herein by reference.

The following examples are offered to illustrate this invention and are not to be construed in any way as limiting the scope of this invention. Unless otherwise stated, all temperatures are in degrees Celsius.

As used herein and in the Figures, the following abbreviations have the following meanings. Any abbreviation not defined below has its generally accepted meaning.

| API | = | American Petroleum Institute |
| ATM EQV | = | atmospheric equivalent |
| EOR Traps | = | end of run traps |
| FID | = | flame ionization detector |
| G | = | grams |
| GC | = | gas chromatography |
| GC/MS | = | gas chromatography/mass spectroscopy |
| HPLC | = | high performance liquid chromatography |
| HYD RDG | = | hydrometer reading |
| MIN | = | minute |
| ML | = | milliliters |
| ODS | = | octadecylsilane |
| pA | = | pico amps |
| ppb | = | parts per billion |
| RI | = | refractive index |
| SFC | = | super critical fluid chromatography |
| SIM DIS | = | simulated distillation |
| ST | = | start |
| TIC | = | total ion current |
| VLT | = | vapor line temperature |
| VOL PCT | = | volume percent |
| WT PCT | = | weight percent |

EXAMPLES

Example 1

Isolation of Cyclohexamantane

The purpose of this example is to demonstrate procedures for the enrichment and isolation of cyclohexamantane. These procedures employed Feedstock B and a pyrolysis step, however this procedure could be facilitated using other materials and without the pyrolysis step. After removal of lower boiling point components (including some lower diamondoid components) from the feedstock by distillation, cyclohexamantane was recovered by chromatography and crystallization. Distillation preferably can be operated to provide specific cuts, thus removing both lower and higher boiling point components, leaving only components within a desired boiling point range. Such fractionation can provide an increased concentration for a desired product within the temperature range.

Figure 4:
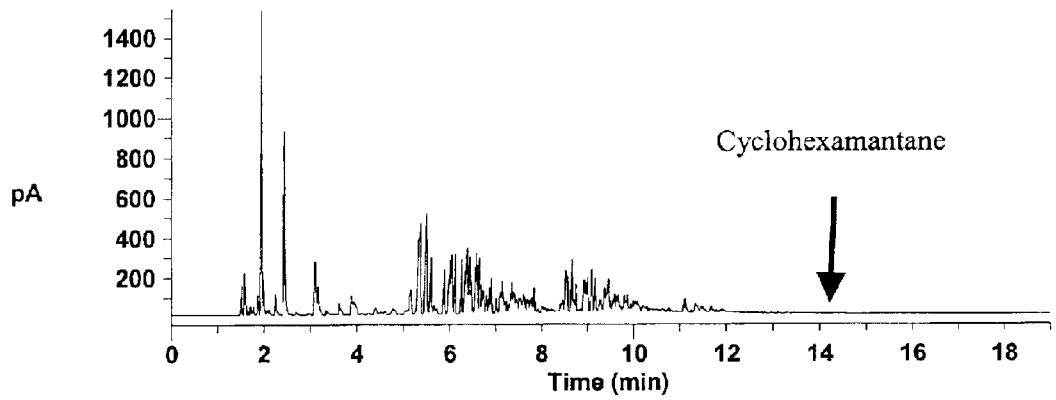
FIG. 4 illustrates the gas chromatogram of a gas condensate feedstock; one of the original feedstocks used in the Examples (Feedstock A). Cyclohexamantane is present at low concentrations, not detectable, but is shown in vacuum distillate fractions (FIG. 7).
Figure 5:
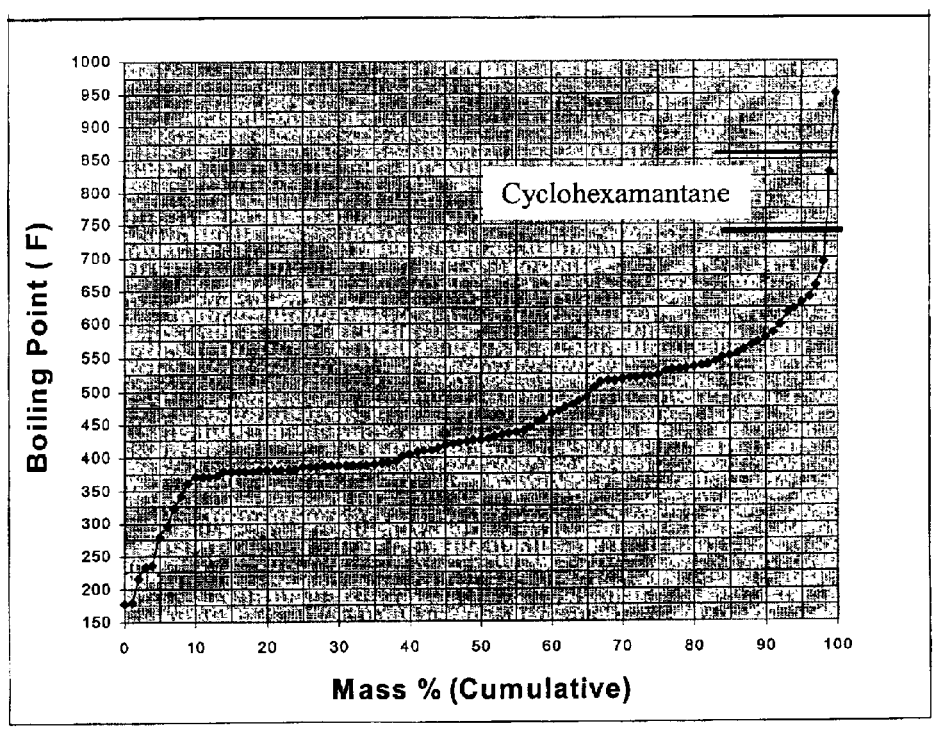
FIG. 5 illustrates a simulated distillation profile of a gas condensate feedstock containing petroleum byproducts used in the Examples (Feedstock B). Boiling points depicted are atmospheric equivalents. Cyclohexamantane was found in the atmospheric residue (650° F.+) of Feedstock B.

Step 1:

Suitable starting materials were obtained. These materials included a gas condensate oil, Feedstock A (a gas chromatogram of this material is depicted in FIG. 4), and a gas condensate oil containing petroleum byproducts Feedstock B (a high temperature simulated distillation profile of this type of material is depicted in FIG. 5). Although other condensates, petroleums, or refinery cuts and product could have been used, these two materials were chosen due to their high diamondoid concentration, approximately 65 percent diamondoids, as determined from GC/MS. Both feedstocks were light colored and had API gravities between 19 and 20° API.

Step 2:

Samples from Feedstocks A and B were distilled into a number of fractions based on boiling point to separate the lower boiling point components (non-diamondoids and lower diamondoids) and for further concentration and enrichment of particular diamondoids in various fractions. The yields of atmospheric distillate fractions of two separate samples of Feedstock B are shown in Table 1, below, and are contrasted to the simulated distillation yields. As seen from Table 1, the simulation data is in agreement with the distillation data.

TABLE 1

Yields of Atmospheric Distillation Fractions from Two Separate Runs of Feedstock B

| Cut (° F.) | Sim Dis Yields (Wt %) | Feedstock B (Run 2) Yields (Wt %) | Difference |
|---|---|---|---|
| To 349 | 8.0 | 7.6 | 0.4 |
| 349 to 491 | 57.0 | 57.7 | −0.7 |
| 491 to 643 | 31.0 | 30.6 | 0.4 |
| 643 and higher | 4.0 | 4.1 | −0.1 |

| Cut (° F.) | Sim Dis Yields (Wt %) | Feedstock B (Run 1) Yields (Wt %) | Difference |
|---|---|---|---|
| To 477 | 63.2 | 59.3 | 3.9 |
| 477 to 515 | 4.8 | 7.3 | −2.5 |
| 515 to 649 | 28.5 | 31.2 | −2.7 |
| 649 and higher | 3.5 | 2.1 | 1.4 |

Figure 6:
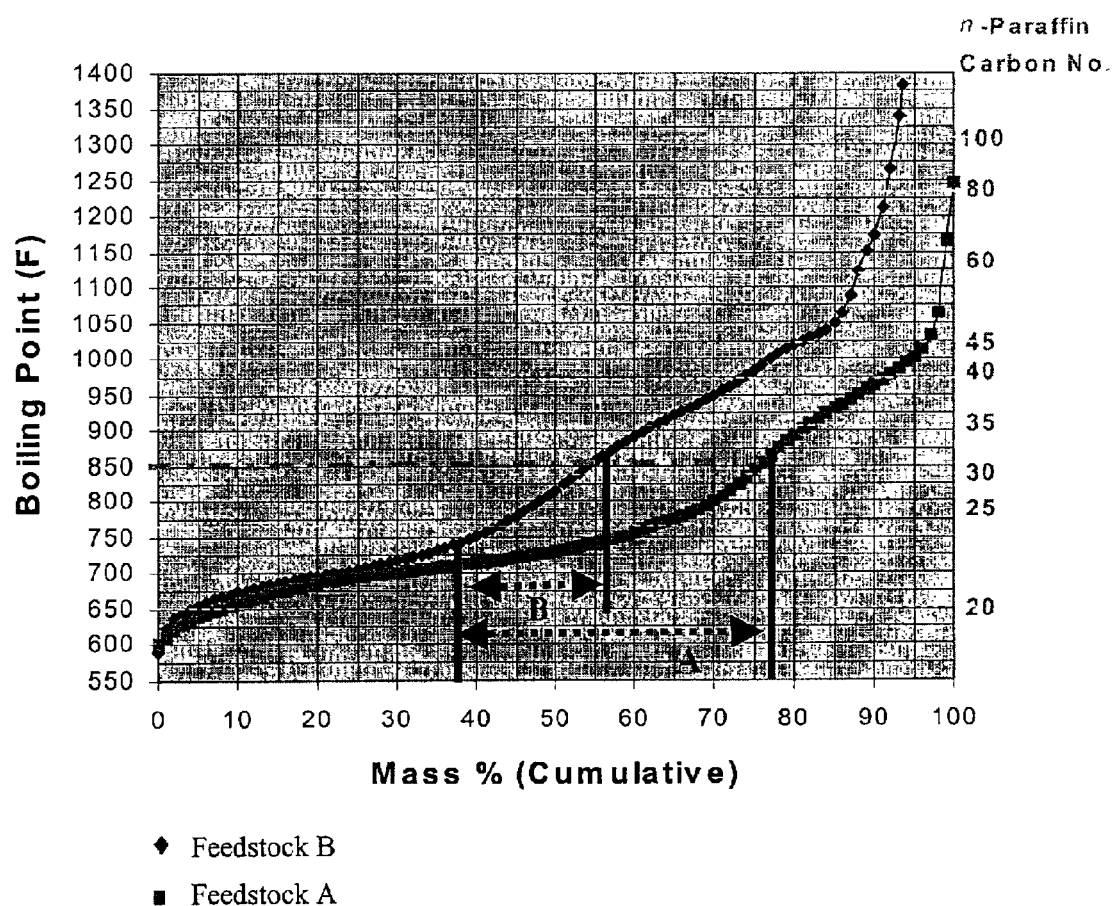
FIG. 6 illustrates a high temperature simulated distillation profile of atmospheric residue of diamondoid rich gas condensates: Feedstock A and Feedstock B. This Figure also illustrates the n-paraffin carbon number atmospheric equivalent boiling points. Labels A and B show the portions of each feedstock which contain cyclohexamantane.

Table 1 shows the yields for atmospheric distillation fractions from two separate runs of Feedstock B and as a comparison the calculated yields for a simulated distillation. As seen from the table, there is a good correlation. FIG. 6 compares a high-temperature simulated distillation profile of the atmospheric residue of the gas condensates, Feedstock A and Feedstock B. Additionally outlined is the identified location and size of the cyclohexamantane-containing fractions. In terms of atmospheric equivalent boiling points the cyclohexamantane components are anticipated to be predominately within the range of about 330 to 550° F. with a large portion within the range of about 395 to 460° F. The non-diamondoid material can be removed by subsequent processes such as pyrolysis.

Figure 7:
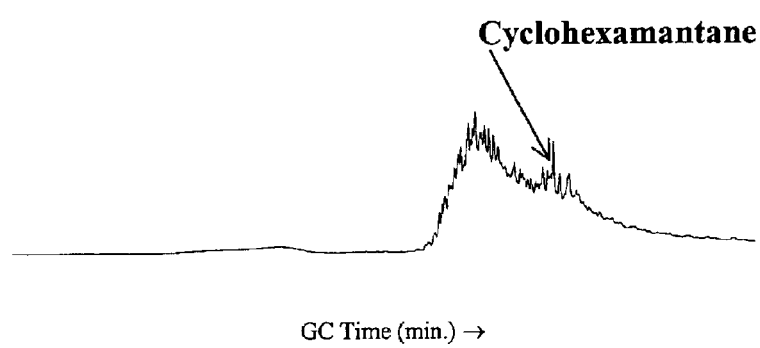
FIG. 7 illustrates a gas chromatographic profile of vacuum distillate residue containing cyclohexamantane and higher diamondoids from a gas condensate, Feedstock A.
Figure 8:
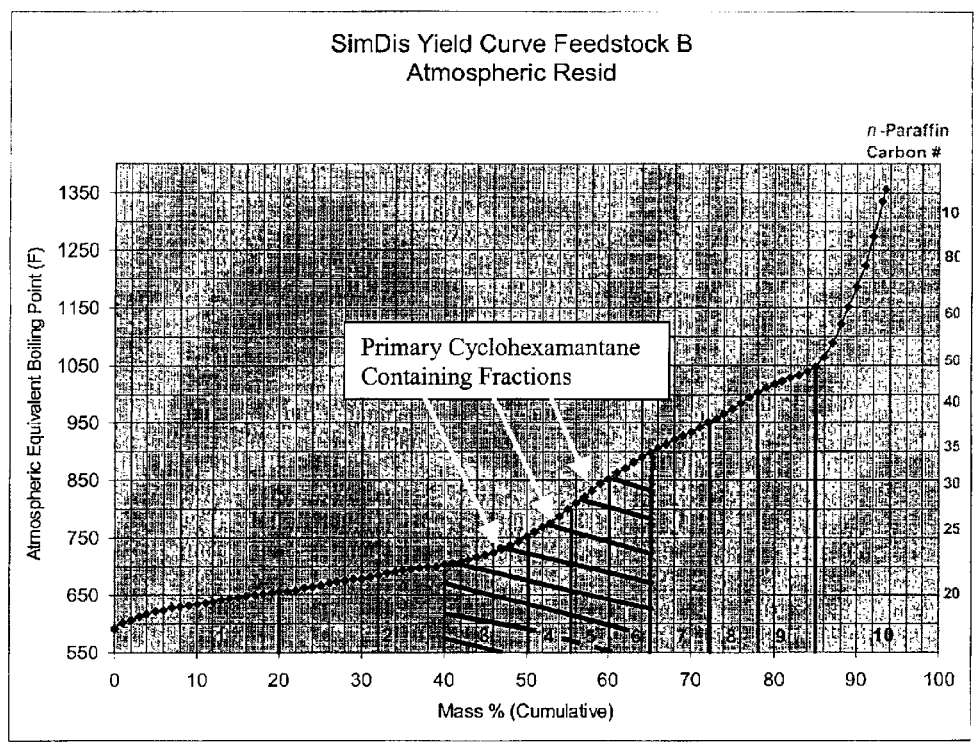
FIG. 8 illustrates a high temperature simulated distillation profile of Feedstock B using the atmospheric distillation 650° F.+ bottoms as feedstock. This figure also illustrates the targeted cut points (1–10) for higher diamondoid isolations. Cyclohexamantane is contained primarily in distillate fractions #3 through #6.
Figure 9:
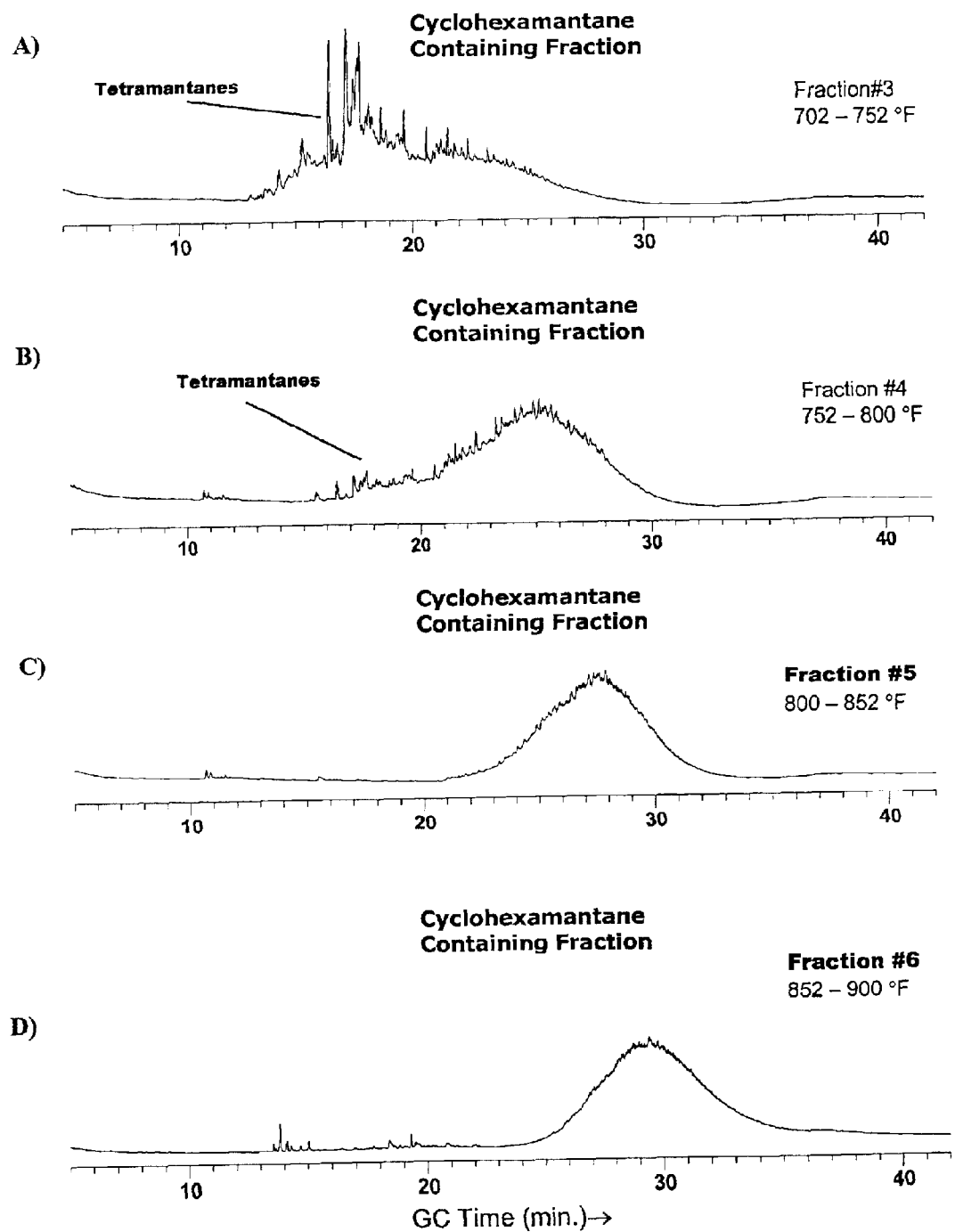
FIGS. 9(A, B, C, D) illustrates the gas chromatograms of vacuum distillate Fractions #3, #4, #5, and #6 of Feedstock B atmospheric distillation 650° F.+ bottoms illustrated in FIG. 8 and exemplified in Example 1.

A sample of gas condensate, Feedstock A was distilled into 38 fractions to remove lower diamondoids and concentrate diamondoids of interest as verified by GC (see FIG. 7) wherein residue left after the distillation of 38 fractions was recovered, predominately boiling in the range of from about 750° F.+ (atmospheric equivalent). The temperature range for these fractions are atmospheric equivalent temperatures, wherein the actual distillation can occur under various conditions including reduced pressure. Additionally, Feedstock B was distilled into fractions containing higher diamondoids guided by high temperature simulated distillation curve (FIG. 8).

TABLE 2A

Distillation Report for Feedstock B (FSL# 8471)
Feedstock B
Column Used: Clean 9" × 1.4" Protruded Packed

| | | DISTILLATION RECORD | | | | NORMALIZED | | ACTUAL | |
|---|---|---|---|---|---|---|---|---|---|
| CUT | VAPOR TEMP ST–END | WEIGHT G | VOLUME ml @ 60° F. | API 60/60 | DENSITY @ 60° F. | WT PCT | VOL PCT | WT PCT | VOL PCT |
| 1 | 226–349 | 67.0 | 80 | 38.0 | 0.8348 | 7.61 | 8.54 | 7.39 | 8.26 |
| 2 | 349–491 | 507.7 | 554 | 22.8 | 0.9170 | 57.65 | 59.12 | 55.98 | 57.23 |
| 3 | 491–643 | 269.6 | 268 | 9.1 | 1.0064 | 30.62 | 28.60 | 29.73 | 27.69 |
| COL HOLDUP | | 0.2 | 0 | 6.6 | 1.0246 | 0.02 | 0.00 | 0.02 | 0.00 |
| BTMS | 643 + | 36.1 | 35 | 6.6 | 1.0246 | 4.09 | 3.74 | 3.98 | 3.62 |
| EOR TRAPS | | 0.0 | 0 | | | 0.00 | 0.00 | | 0.00 |
| TOTALS | | 880.6 | 937 | | | 100.00 | 100.00 | 97.09 | 96.80 |
| LOSS | | 26.4 | 31 | | | | | 2.91 | 3.20 |
| FEED | | 907.0 | 968 | 19.5 | 0.9371 | | | 100.00 | 100.00 |
| BACK CALCULATED API AND DENSITY | | | | 19.1 | 0.9396 | | | | |

TABLE 2B

Distillation Report for Feedstock B (FSL# 8471)
Feedstock B
Column Used: Clean 9" × 1.4" Protruded Packed

| TEMPERATURE DEGREES F. | | | | | | | | API GRAVITIES | | |
|---|---|---|---|---|---|---|---|---|---|---|
| VAPOR | | | | | | | | OBSERVED | | |
| VLT | ATM EQV. | POT | PRESSURE TORR | REFLUX RATIO | CUT NO | VOLUME ml @ 60°F. | WEIGHT G | HYD RDG | TEMP ° F. | 60° F. |
| 93 | 225.8 | 262 | 50.000 | 3:1 | | | START OVERHEAD | | | |
| 198 | 349.1 | 277 | 50.000 | 3:1 | 1 | 80 | 67.0 | 39.6 | 80.0 | 38.0 |
| 321 | 490.8 | 376 | 50.000 | 3:1 | 2 | 554 | 507.7 | 24.1 | 80.0 | 22.8 |
| Cut 2 looks Milky, White crystals form in Run Down Line. Heat Lamp applied to drip tube. | | | | | | | | | | |
| Cool to transfer btms to smaller flask. | | | | | | | | | | |
| 208 | 437.7 | 323 | 10.000 | 3:1 | | | START OVERHEAD | | | |
| 378 | 643.3 | 550 | 10.000 | 3:1 | 3 | 268 | 269.6 | 9.9 | 75.0 | 9.1 |
| | | | Shutdown due to dry pot | | | | | | | |
| | | | END OF RUN TRAPS | | | 0 | 0.0 | | | |
| | | | VOLUME DISTILLED | | | 902 | | | | |
| | | | COLUMN HOLDUP | | | 0 | 0.2 | 0.0 | 0.0 | 6.6 |
| | | | BOTTOMS | | | 35 | 36.1 | 7.2 | 72.0 | 6.6 |
| | | | RECOVERED | | | 937 | 880.6 | | | |
| | | | FEED CHARGED | | | 968 | 907.0 | 20.7 | 80.0 | 19.5 |
| | | | LOSS | | | 31 | 26.4 | | | |

TABLE 3A

Vacuum Distillation Report for Feedstock B (FSL# 8691)
Feedstock B - Atmospheric distillation resid 650° F. + bottoms
Column Used: Sarnia Hi Vac

| | TEMPERATURE DEGREES F. | | | | | | | API GRAVITIES | |
|---|---|---|---|---|---|---|---|---|---|
| VAPOR | | | | | | | | OBSERVED | |
| VLT | ATM EQV. | POT | PRESSURE TORR | REFLUX RATIO | CUT NO | VOL ml 60° F. | WEIGHT G | HYD RDG | TEMP ° F. | 60° F. |

| VLT | ATM EQV. | POT | PRESSURE TORR | REFLUX RATIO | CUT NO | VOL ml 60° F. | WEIGHT G | HYD RDG | TEMP ° F. | 60° F. |
|---|---|---|---|---|---|---|---|---|---|---|
| 315 | 601.4 | 350 | 5.000 | | | | START OVERHEAD | | | |
| 344 | 636.8 | 382 | 5.000 | | | 300 | READING | | | |
| 342 | 644.9 | 389 | 4.000 | | | 500 | READING | | | |
| 344 | 656.3 | 395 | 3.300 | | 1 | 639 | 666.4 | 7.8 | 138.0 | 4.1 |
| 353 | 680.1 | 411 | 2.500 | | | 400 | READING | | | |
| 364 | 701.6 | 430 | 2.100 | | 2 | 646 | 666.9 | 9.4 | 138.0 | 5.6 |
| 333 | 736.0 | 419 | 0.400 | | | 200 | READING | | | |
| 336 | 751.9 | 432 | 0.300 | | 3 | 330 | 334.3 | 12.4 | 139.0 | 8.3 |
| 391 | 799.9 | 468 | 0.500 | | 4 | 173 | 167.7 | 19.0 | 139.0 | 14.5 |
| 411 | 851.6 | 500 | 0.270 | | 5 | 181 | 167.3 | 26.8 | 139.0 | 21.7 |
| 460 | 899.8 | 538 | 0.360 | | 6 | 181 | 167.1 | 27.0 | 139.0 | 21.9 |
| 484 | 950.3 | 569 | 0.222 | | 7 | 257 | 238.4 | 26.2 | 139.0 | 21.2 |

Shut down distillation to check pot temperature limits with customer. (Drained trap material 5.3 grams)

| VLT | ATM EQV. | POT | PRESSURE TORR | REFLUX RATIO | CUT NO | VOL ml 60° F. | WEIGHT G | HYD RDG | TEMP ° F. | 60° F. |
|---|---|---|---|---|---|---|---|---|---|---|
| 472 | 935.7 | 576 | 0.222 | | | | START OVERHEAD | | | |
| 521 | 976.3 | 595 | 0.340 | | 8 | 91 | 85.4 | 23.7 | 139.0 | 18.9 |
| 527 | 999.9 | 610 | 0.235 | | 9 | 85 | 80.8 | 23.0 | 139.0 | 18.2 |
| 527 | 1025.6 | 624 | 0.130 | | 10 | 98 | 93.8 | 21.6 | 139.0 | 16.9 |

Drained remaining trap material of 16.5 grams (~4 grams of water)

| | | | | | | | | | | |
|---|---|---|---|---|---|---|---|---|---|---|
| | MID AND | END OF RUN TRAPS | | | | 20 | 17.8 | (mathematically combined) | | |
| | | VOLUME DISTILLED | | | | 2701 | | | | |
| | | COLUMN HOLDUP | | | | 4 | 4.0 | 0.0 | 0.0 | 3.4 |
| | | BOTTOMS | | | | 593 | 621.8 | 11.0 | 214.0 | 3.4 |
| | | RECOVERED | | | | 3298 | 3311.7 | | | |
| | | FEED CHARGED | | | | 3298 | 3326.3 | 18.0 | 234.0 | 8.6 |
| | | LOSS | | | | −5 | 14.6 | | | |

TABLE 3B

Distillation Report for Feedstock B-btms (FSL# 8691)
Feedstock B - Atmospheric distillation resid 650° F. + bottoms
Column Used: Sarnia HiVac

| CUT | VAPOR TEMP ST–END | WEIGHT G | VOLUME ml @ 60° F. | API 60/60 | DENSITY 60° F. | WT PCT | VOL PCT | WT PCT | VOL PCT |
|---|---|---|---|---|---|---|---|---|---|
| 1 | 601–656 | 666.4 | 639 | 4.1 | 1.0435 | 20.12 | 19.38 | 20.03 | 19.40 |
| 2 | 656–702 | 666.9 | 646 | 5.6 | 1.0321 | 20.14 | 19.59 | 20.05 | 19.62 |
| 3 | 702–752 | 334.3 | 330 | 8.3 | 1.0122 | 10.09 | 10.01 | 10.05 | 10.02 |
| 4 | 752–800 | 167.7 | 173 | 14.5 | 0.9692 | 5.06 | 5.25 | 5.04 | 5.25 |
| 5 | 800–852 | 167.3 | 181 | 21.7 | 0.9236 | 5.05 | 5.49 | 5.03 | 5.50 |
| 6 | 852–900 | 167.1 | 181 | 21.9 | 0.9224 | 5.05 | 5.49 | 5.02 | 5.50 |
| 7 | 900–950 | 238.4 | 257 | 21.2 | 0.9267 | 7.25 | 7.79 | 7.17 | 7.80 |
| 8 | 950–976 | 85.4 | 91 | 18.9 | 0.9408 | 2.58 | 2.76 | 2.57 | 2.76 |
| 9 | 976–1000 | 80.8 | 85 | 18.2 | 0.9452 | 2.44 | 2.58 | 2.43 | 2.58 |
| 10 | 1000–1026 | 93.8 | 98 | 16.9 | 0.9535 | 2.83 | 2.97 | 2.82 | 2.98 |
| COL HOLDUP | | 4.0 | 4 | 3.4 | 1.0489 | 0.12 | 0.12 | 0.12 | 0.12 |
| BTMS | 1026 + | 621.8 | 593 | 3.4 | 1.0489 | 18.78 | 17.98 | 18.69 | 18.01 |
| EOR TRAPS | | 17.8 | 20 | | | 0.54 | 0.61 | 0.54 | 0.61 |
| TOTALS | | 3311.7 | 3298 | | | 100.00 | 100.00 | 99.56 | 100.15 |
| LOSS | | 14.6 | −5 | | | | | 0.44 | −0.15 |
| FEED | | 3326.3 | 3293 | 8.6 | 1.0100 | | | 100.00 | 100.00 |
| BACK CALCULATED API & DENSITY | | | | 9.4 | 1.0039 | | | | |

TABLE 4

Elemental Composition of Feedstock B

Analyses on Feedstock B Atmospheric Distillation 650+ F. Resid

| Measured | Value |
| --- | --- |
| Nitrogen | 0.991 wt % |
| Sulfur | 0.863 wt % |
| Nickel | 8.61 ppm |
| Vanadium | <0.2 ppm |

Table 4 illustrates the elemental composition of Feedstock B atmospheric distillation (650° F.+) residue including some of the identified impurities. Table 4 displays the weight percent nitrogen, sulfur, nickel and vanadium present within this feedstock. These materials are removed in subsequent steps.

Step 3:

Removal of Non-diamondoids Using Pyrolysis

Figure 10:
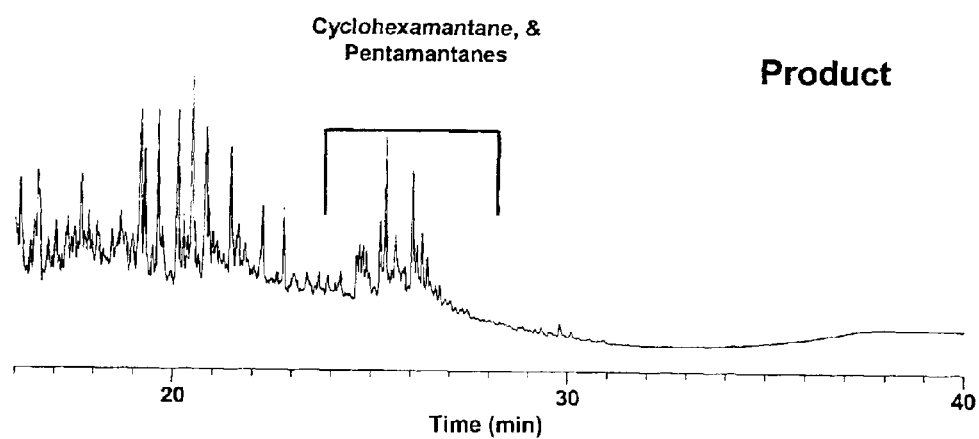
FIGS. 10(A,B) illustrates the gas chromatograms of the concentration of hexamantanes using pyrolysis.
Figure 10:
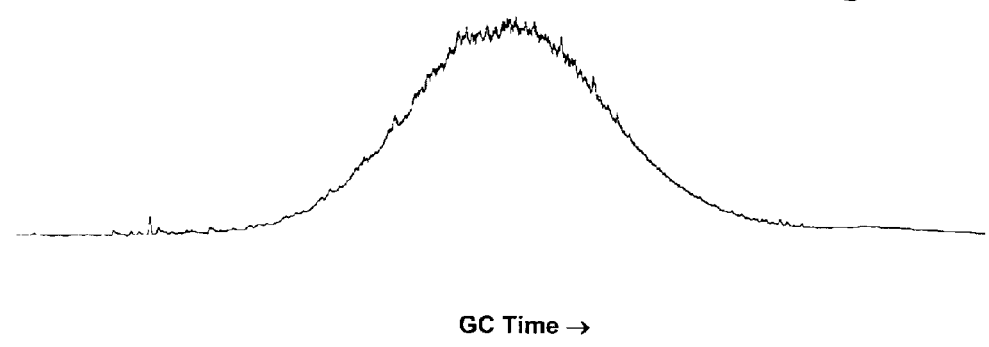

This step, although not necessary for the recovery of cyclohexamantane from some starting materials such as feedstock A, is either necessary or greatly facilitates cyclohexamantane recovery from other feedstocks, e.g. Feedstock B. We used a sealed, evacuated reactor to pyrolyze and degrade a portion of the non-diamondoid components while enriching the diamondoids in the residue. Such reactors can operate at a variety of temperatures and pressures. FIGS. 10(A,B) illustrate this method and show a gas chromatogram of the Feedstock B 650° F.+ distillation fraction 5 before pyrolysis and the resulting pyrolysis product. Prior to pyrolysis, the hexamantane peaks are obscured by the presence of non-diamondoid components. Pyrolysis can be used to degrade the non-diamondoid components to easily removable gas and coke like solids. As shown in FIG. 10A, the hexamantane peaks are clearly visible after pyrolysis.

A PARR® reactor, from PARR INSTRUMENT COMPANY, Moline, Ill., was used to process the distillation fractions obtained from vacuum distillation of a feedstream. For this example, Feedstock B 650° F.+ distillation fraction 5 was used as a feedstock for pyrolysis. Pyrolysis was then conducted on 5.2 grams of this sample by heating the sample under vacuum in a vessel at 450° C. for 16.7 hours.

Step 4:

The higher diamondoid components enriched following the distillation of Step 2 and the pyrolysis of Step 3 (if needed), were further isolated to a cyclohexamantane fraction in the following way. In one case the distillation fraction of Feedstock A containing cyclohexamantane (i.e., the residue left after vacuum distillation fraction 38; a GC profile identifying this fraction is shown in FIG. 6) was passed through a silica-gel gravity chromatography column to remove polar compounds and asphaltenes. The use of a silver nitrate impregnated silica gel provides cleaner diamondoid-containing fractions by removing the free aromatic and polar components. While it is not necessary to use this chromatographic aromatic separation method, it facilitates subsequent steps.

Alternatively, a pyrolysis product of a distillate fraction of Feedstock B could be passed through a silica-gel gravity chromatography column to remove polar compounds and asphaltenes. The use of a silver nitrate impregnated silica gel provides cleaner diamondoid-containing fractions by removing the free aromatic and polar components. In either instance, the distillate fraction or the pyrolysis products could be purified using this step prior to subsequent isolation procedures.

Step 5:

HPLC was used to provide sufficient enrichment of cyclohexamantane to allow for its crystallization. Suitable columns for use are well known to those skilled in the art. In some cases, reverse-phase HPLC with acetone as mobile phase can be used to effect this purification. A preparative ODS HPLC run of Feedstock B distillate cut 6 pyrolysis product saturated hydrocarbon fraction was performed and the HPLC chromatogram recorded using a differential refractometer: elution fractions for cyclohexamantane are shown in FIG. 11. The "x" marks the fraction (#23) which contains the highest concentration of cyclohexamantane.

The HPLC columns used were two 50 cm×20 mm I.D. WHATMAN octadecyl silane (ODS) columns operated in series (Whatman columns are manufactured by Whatman Inc., USA). A 500 microliter sample of a solution of the cut 6 pyrolysis product saturated hydrocarbon fraction (54 mg) was injected into the columns. The columns were set-up using acetone at 5.00 ml/min as a mobile phase carrier. HPLC fractions 23–26 reached the purity (FIGS. 12 A,B) necessary for cyclohexamantane to crystallize. FIGS. 13A,B illustrates photomicrographs of representative cyclohexamantane crystals precipitated from ODS HPLC fractions #23–26. The other cyclohexamantane components in this fraction could be separated using further chromatographic techniques including preparative gas chromatography or more preferably additional HPLC runs using columns of different selectivity as outlined below. Additionally other techniques known in the crystallization art could be utilized including but not limited to fractional sublimation, progressive recrystallization or zone refining.

Step 6:

After obtaining crystals of suitable size, cyclohexamantane could be sent for structural determination using X-ray diffraction.

Example 2

Figure 12:
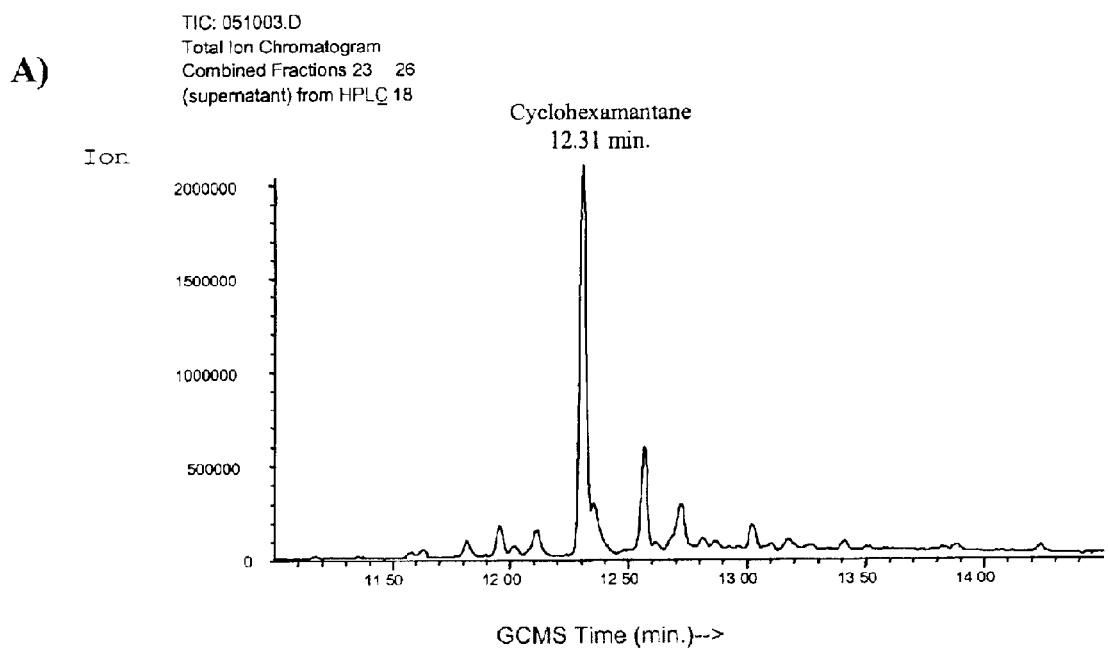
FIGS. 12(A,B) illustrates GC/MS total ion chromatogram (TIC) and mass spectrum of ODS BPLC cyclohexamantane-containing fractions #23–26.
Figure 12:
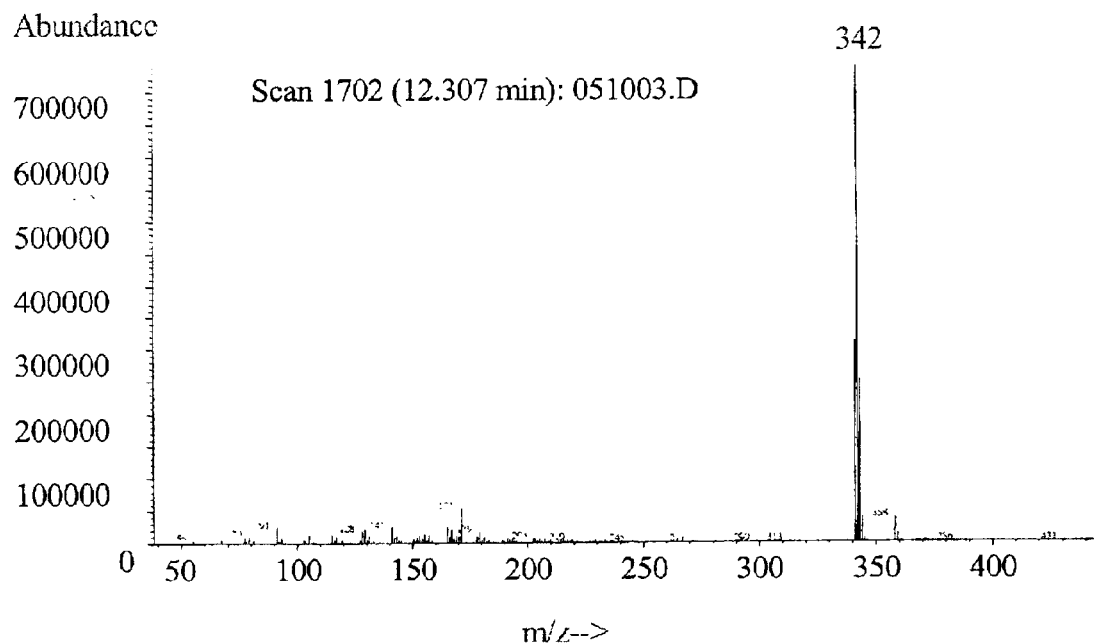

Isolation of Cyclohexamantane Using Two HPLC Columns with Different Selectivities As shown in Example 1, cyclohexamantane can be isolated in high purity using BPLC methods. In this example, HPLC columns of different selectivities were used in succession to isolate cyclohexamantane. FIG. 12 shows results of a preparative separation of cyclohexamantane from distillation cut 6-pyrolysis product saturated hydrocarbon fraction using an octadecyl silane (ODS) BPLC column with acetone as a mobile phase. This first HPLC system consisted of two Whatman M20 10/50 ODS columns operated in series using acetone as mobile phase at 5.00 mL/min. The detector used was a differential refractometer. From this HPLC run, fractions #23–26 (FIG. 12A) were combined and taken for further purification on a second HPLC system. This combined fraction contained cyclohexamantane.

Figure 14:
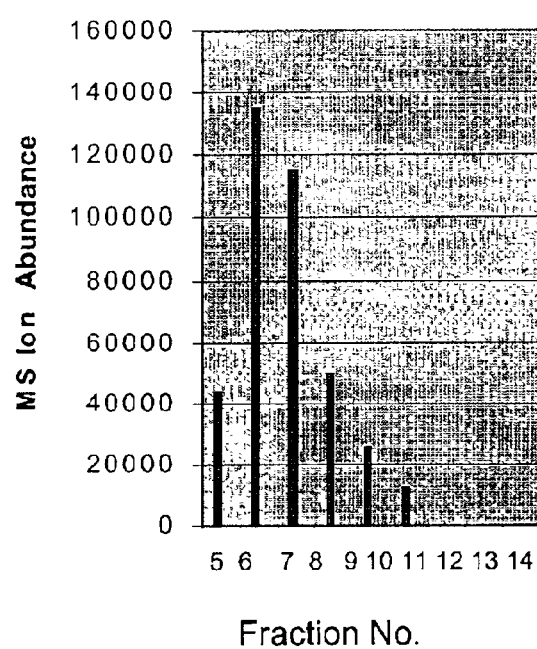
FIG. 14 illustrates results of a BPLC separation using Hypercarb stationary phase of ODS HPLC fractions #23–26 (FIG. 12). Cyclohexamantane is found in Hypercarb BPLC fractions #5–11.

Further purification of combined ODS HPLC fractions #23–26 was achieved using a HYPERCARB stationary phase HPLC column which has a different selectivity in the separation of cyclohexamantane than the ODS column discussed above. FIG. 14 shows a preparative Hypercarb HPLC run indicating elution time of cyclohexamantane.

Figure 13:
FIGS. 13(A,B) illustrates photomicrographs of cyclohexamantane crystals which precipitated from ODS HPLC fractions #23–26 (FIG. 14).
Figure 13:
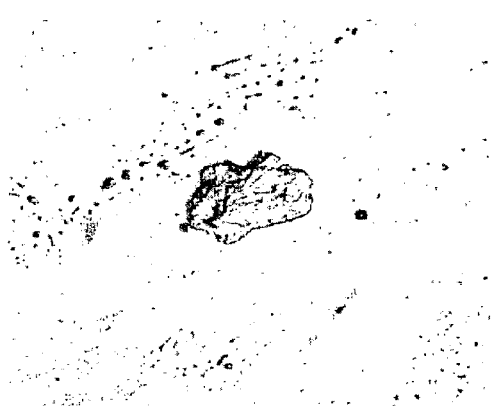

Using this method, a 50 microliter sample of approximately 1 mg of ODS HPLC combined fraction #23–26 in acetone was injected into the Hypercarb column, 10 mm I.D.×250 mm, operated using acetone at 3.00 mL/min as mobile phase (@480 psi), and using a differential refracto meter detector. While ODS HPLC fraction #23–26 was being prepared for injection in the HPERCARB HPLC system, some of the cyclohexamantane in the fraction spontaneously precipitated as a fine white powder which would dissolve only slightly in cyclohexane solvent. GCMS analysis showed this precipitate to be cyclohexamantane. Photomicrographs of the fine crystalline particles in the precipitate are shown in FIG. 13.

Figure 15:
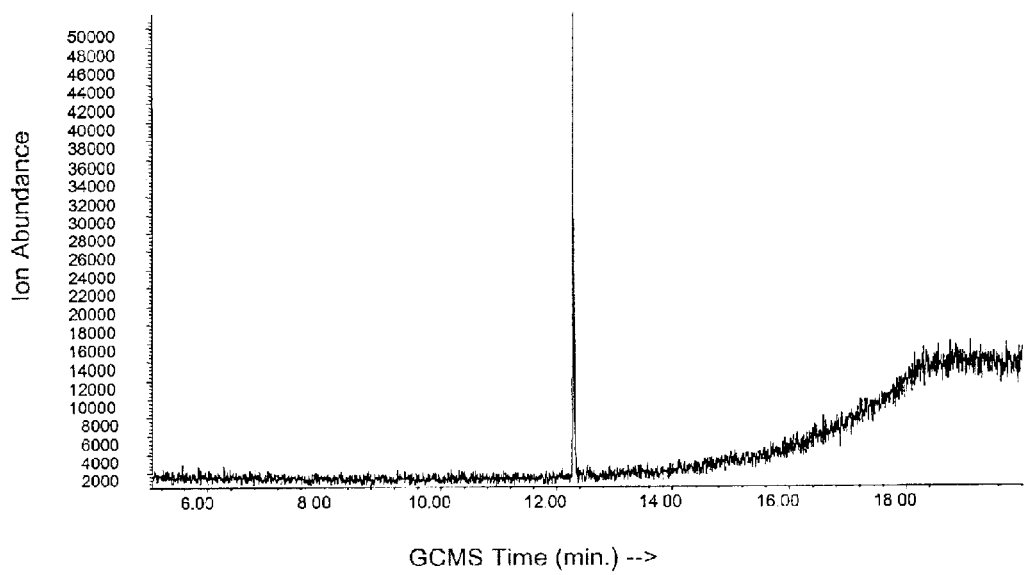
FIGS. 15(A,B) illustrates the GC/MS total ion chromatogram and mass spectrum of cyclohexamantane isolated by HPLC using ODS followed by Hypercarb stationary phase columns.
Figure 15:
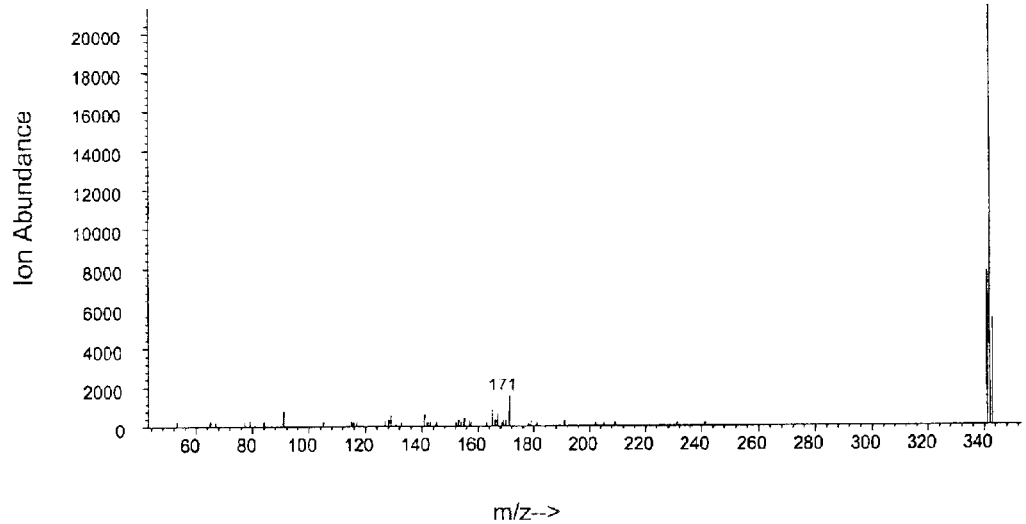
Figure 16:
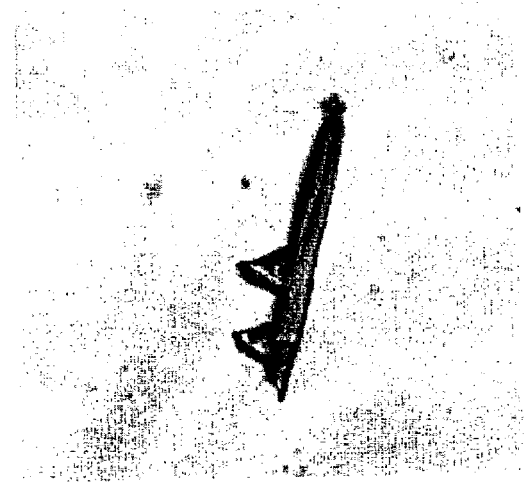
FIGS. 16(A,B) illustrates photomicrographs of cyclohexamantane crystals precipitated from Hypercarb HPLC fractions #6–9 characterized in FIG. 15.
Figure 16:
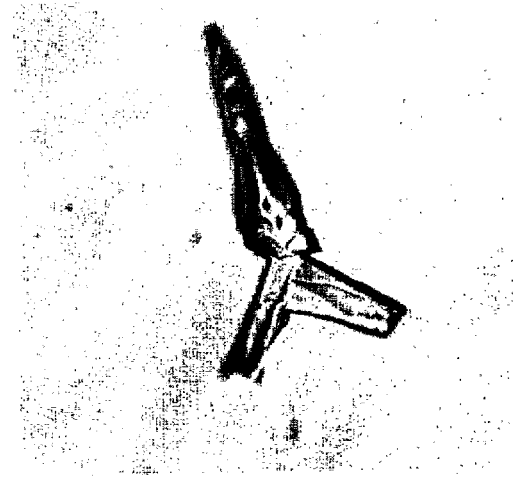

Hypercarb HPLC fractions were taken resulting in the isolation and subsequent crystallization of cyclohexamantane (FIGS. 15A,B). Photomicrographs of representative crystals of cyclohexamantane obtained by this method are shown in FIGS. 16A,B. After obtaining crystals of suitable size, cyclohexamantane could be sent for structural determination using X-ray diffraction.

What is claimed is:

1. A composition comprising at least about 5 percent by weight cyclohexamantane based on the total weight of the composition.

2. The composition of claim 1, wherein the cyclohexamantane comprises about 50 to 100 percent by weight based on the total weight of the composition.

3. The composition of claim 1, wherein the cyclohexamantane comprises about 70 to 100 percent by weight based on the total weight of the composition.

4. The composition of claim 1, wherein the cyclohexamantane comprises about 95 to 100 percent by weight based on the total weight of the composition.

5. The composition of claim 4, wherein the composition comprises cyclohexamantane in crystalline form.

* * * * *